(12) United States Patent
Bakaltcheva (10) Patent No.: US 8,349,367 B2
(45) Date of Patent: Jan. 8, 2013

(54) FREEZE-DRIED PLASMA FORMATS FOR THE TRAUMA CARE FIELD

(76) Inventor: Irina B. Bakaltcheva, Springfield, VA (US)

( * ) Notice: Subject to any disclaimer, the term of this patent is extended or adjusted under 35 U.S.C. 154(b) by 334 days.

(21) Appl. No.: 12/681,866

(22) PCT Filed: Oct. 14, 2008

(86) PCT No.: PCT/US2008/079859
§ 371 (c)(1), (2), (4) Date: Apr. 6, 2010

(87) PCT Pub. No.: WO2009/049318
PCT Pub. Date: Apr. 16, 2009

(65) Prior Publication Data
US 2010/0233671 A1    Sep. 16, 2010

Related U.S. Application Data

(60) Provisional application No. 60/998,928, filed on Oct. 12, 2007.

(51) Int. Cl.
*A61K 35/16* (2006.01)

(52) U.S. Cl. ........................................ 424/530

(58) Field of Classification Search ............... None
See application file for complete search history.

(56) References Cited

U.S. PATENT DOCUMENTS

| | | |
|---|---|---|
| 6,358,678 B1 | 3/2002 | Bakaltcheva |
| 6,436,705 B1 | 8/2002 | Bakaltcheva |
| 6,541,518 B2 | 4/2003 | Shanebrom |
| 6,905,612 B2 | 6/2005 | Dorian et al. |
| 7,931,919 B2 | 4/2011 | Bakaltcheva |
| 2002/0127535 A1 | 9/2002 | Bakaltcheva |
| 2006/0247426 A1 | 11/2006 | Bardat |
| 2007/0166389 A1 | 7/2007 | Bakaltcheva |
| 2008/0119818 A1 | 5/2008 | Bakaltcheva |
| 2010/0273141 A1 | 10/2010 | Bakaltcheva |

FOREIGN PATENT DOCUMENTS

DE    3321 200    * 12/1984
WO    WO 96/17871    6/1996

OTHER PUBLICATIONS

Yang et al., "Alanine-Glutamine Dipeptide (AGD) Inhibits Expression of Inflammation-Related Genes in Hemorrhagic Shock", J. Parenteral and Enteral Nutrition 31 (1) : 32-36 (2007).*
Erber et al., "Plasma and plasma products in the treatment of massive haemorrhage", Best Practice & Research Clinical Haematology 19 (1) : 97-112 (2006).*
PCT Search Report of Jul. 30, 2009.
PCT Patentability Report of Jul. 30, 2009.
I.B. Bakaltcheva et al., Thrombin Research 120:105-116 (2007).
M. Majetschak et al., J. Trauma 56:991-1000 (2004).
B. Bakalar et al., Crit. Care Med. 34(2):381 (2006).
J.D. Paauw et al., Am. J. Clin, Nutr. 60:203-6 (1994).
M. Malgorzata et al., Blood Coagulation and Fibrinolysis 18(7):689 (2007).
E.A. Gonzalez et al., J. Trauma 62:112-119 (2007).
B. Horowitz et al., Blood 79(4826-31 (1992).
B.S. Zuokerbraun et al., Shock 23(6):527-32 (2005).
R. Exner et al., Annals of Surgery 237(1):110-115 (2003).
T. Grieb et al., Biologicals 30:207-216 (2002).
B.H. Tieu et al., World of Surgery 31:1055-1064 (2007).
J.W. Lee et al., J. Mol. Cell. Cardiology 31:113-121 (1999).
H.M. Zbikowske et al., Free Radical Biology and Medicine 40:536-42 (2006).

* cited by examiner

*Primary Examiner* — Sandra Saucier
(74) *Attorney, Agent, or Firm* — Remenick PLLC (57) ABSTRACT

Disclosed are freeze-dried plasma formats specifically designed for the trauma care field. Blood plasma is subjected to a glucose removal step, a protein fraction up-concentration step and addition of stabilizers prior to freeze-drying. Preferable stabilizers are glutamine dipeptides, glutamine and glycine. The glutamine based formulation is added direct to plasma and serves three main purposes: 1) Increases stability of plasma proteins and stabilizes pH in freeze-dried state; 2) Increases stability of plasma proteins against Gamma Irradiation and thus allows for the application of a terminal sterilization step; 3) Introduces supplements beneficial to the trauma patient.

26 Claims, 3 Drawing Sheets

FREEZE-DRIED PLASMA FORMATS FOR THE TRAUMA CARE FIELD

REFERENCE TO RELATED APPLICATIONS

This application claims priority to U.S. Provisional Application No. 60/998,928 entitled "Freeze-Dried Plasma Formats for the Trauma Care Field" filed Oct. 12, 2007, and to International Application No. PCT/US2008/79859, filed Oct. 14, 2008, the entirety of each of which is hereby incorporated by reference.

RIGHTS IN THE INVENTION

This invention was made with support from the United States Government and, specifically, the Walter Reed Army Institute of Research and, accordingly, the United States government has certain rights in this invention.

BACKGROUND OF THE INVENTION

1. Field of the Invention

This invention relates generally to plasma containing compositions and methods for sterilizing and preserving plasma for storage and transportation at ambient temperatures. The plasma compositions are designed specifically for the trauma care field.

2. Description of the Background Fresh frozen plasma (FFP) is essential for the clinical management of coagulopathies associated with combat trauma. However, a frozen formulation has three major limitations: (a) FFP must be kept frozen at about minus 18° C. or below; (b) the number of FFP units transshipped is restricted by the dry ice ($CO_2$) volume and/or weight limitations of transport; (c) thawing time of intact plasma units is generally 30 to 40 minutes.

Clearly, the limitations of the frozen formulation reduce plasma availability in the field, or in rural locations, for both logistic and practical laboratory reasons. A freeze-dried formulation, alternatively, could remedy the storage and shipment problem by converting liquid plasma into a lightweight, solid product that is stable at ambient temperature. Currently, the advantage of using freeze-dried plasma verses frozen plasma has been mostly recognized in developing countries [1] and [2]. There are limitations in facilities for preparation, transportation and storage of frozen blood products in most of these countries. Therefore, freeze-dried products with less storage and transportation requirements are preferred.

Pooled plasma was lyophilized for the first time during World War II. However, it was discovered that the process of freeze-drying does not kill viruses in plasma. In addition, the use of plasma from large pools carried an unacceptable risk of transmitting pathogens [3]. Consequently, the production of freeze-dried plasma was abandoned.

Several methods for pathogen inactivation in plasma are now at different stages of development. Such methods are based on: solvent/detergent treatment [4]; utilization of vitamin B2, riboflavin and light [5] application of psoralens and UV light [6]. The current endeavor is to freeze-dry pathogen-inactivated plasma products. These products will guarantee both unconstrained plasma availability and safety. Several groups report stability results for freeze-dried, pathogen-inactivated, solvent/detergent (SD)-treated plasma products. Hellstern et al. describe the production of freeze-dried and deep-frozen batches of SD plasma, and characterize the product in vitro [7]. Clotting factors activities were found to decrease more markedly in the freeze-dried plasmas than in the deep-frozen batches. Storage stability data at ambient temperature are not reported in this study [7]. The German Red Cross introduced a freeze-dried pathogen-inactivated SD plasma product in 1990. The product was examined to determine whether the quality was comparable to standard preparations. It was determined that freeze-dried SD plasma did not fulfill basic requirements. The time required to reconstitute the lyophilized product was too long. Also, the resultant pH values of the lyophilized/reconstituted plasma were close to the alkaline range; thus, considerable changes in blood gas and electrolyte levels were to be expected in the recipient [8]. In a separate study, the quality of three conventional fresh-frozen plasma preparations and one freeze-dried SD plasma preparation were compared [9]. Coagulation activity was significantly reduced in the freeze-dried SD plasma [9]. Storage stability data at ambient temperature are not reported in these studies [8] and [9]. In Thailand, freeze-dried plasma has been used by hemophilia patients as an in home treatment product since 1982. The chemical and coagulation properties of this product are reported nearly the same as FFP after reconstitution with sterile water [1]. The clinical effectiveness of this product has been shown in hemophilia patients with bleeding episodes. However, storage of the freeze-dried plasma product is still confined to 4° C. and requires refrigeration equipment [2].

Bakaltcheva et al. developed a method for production of freeze-dried whole plasma with increased stability at ambient temperature, physiological pH and osmolality [10]. Briefly, plasma supplemented with 60 mM sucrose, trehalose, mannitol, sorbitol or glycine was freeze-dried. The samples were subjected to forced degradation at 40 C for 10 days in order to quickly evaluate the effectiveness of the different stabilizers. Initial PT, APTT and TT values were 14.4 d 0.5 s, 31.4±1.5 s and 18.3±0.6 s, respectively. At the end of the degradation period, PT, APTT and TT were substantially prolonged. In the presence of glycine, at the end of the degradation period, PT, APTT and TT values remained close to the initial values and were 15.5±0.4 s, 35.7±0.9 s and 19.4±0.2 s, respectively. All tested stabilizers provided protection. Glycine, however, outperformed all tested polyols, providing superior preservation of plasma clotting properties. The process of freeze-drying caused a complete loss of plasma $pCO_2$ (gas) and a substantial increase in plasma pH. Citric and ascorbic acid were found to be suitable pH adjusters for lyophilized/rehydrated plasma. However, the aim of this work was limited to the development of a method for production of freeze-dried whole plasma with increased stability, physiological pH and osmolality. A suitable pathogen inactivation method is to be combined with the lyophilization technology in order to increase the safety and availability of human plasma in rural areas and austere environments.

Gamma irradiation effectively inactivates all known blood-borne viruses and is currently explored vigorously as a pathogen inactivation method for plasma derivatives [11]. However, its application at virucidally effective doses (50 kGy) to frozen plasma products results in unacceptable losses in functional activity [11]. Ascorbate is the most commonly used protectant for plasma proteins against gamma irradiation [11-13]. However other antioxidants/stabilizers may be important when a high irradiation dose is applied. Grieb T et al. reported that the loss of protein activity after application of high dose gamma irradiation can be controlled [14]. Control is achieved by a combination of protection through the use of the antioxidant ascorbate and by freeze-drying to minimize the potential for generating free radicals.

Trauma induced coagulopathy is associated with an extremely high mortality. Transfusion of blood components remains the main treatment approach, with some recent studies advocating a more aggressive use of fresh frozen plasma (FFP) [15-16]. Most of the battlefield deaths take place before reaching a medical facility. Therefore, there is a clear need for the development of innovative and effective strategies for the early (pre-hospital) treatment of coagulopathy. One solution is to utilize freeze-dried, shelf-stable plasma, which has been subjected to a reliable pathogen inactivation method. However, such freeze-dried plasma has to be specifically designed to meet the needs of the trauma patient. Hemodilution, hypothermia, acidosis, tissue hypoperfusion and consumption of clotting factors are common reasons for the development of coagulopathy in trauma patients [17]. Once a stabilizer-supplemented freeze-dried plasma is liquefied upon reconstitution and administered to a patient, the stabilizer will be available to exercise its protective properties within the complex context of the specific injury or disease being treated. Therefore, when formulating freeze-dried plasma for use in the trauma care field, one should consider the complex state of a trauma patient and utilize stabilizers, which will support and not retard the recovery of the trauma patient.

There is a need to develop a method for production of freeze-dried whole plasma with increased stability at ambient temperature, physiological pH and osmolality.

SUMMARY OF THE INVENTION

This invention is broadly directed to plasma containing compositions and methods for sterilizing and preserving plasma for storage and transportation at ambient temperatures. The plasma compositions are designed specifically for the trauma care field.

One embodiment of the invention is directed to compositions comprising fresh plasma or fresh frozen plasma containing an up-concentrated protein fraction or an up-concentrated platelet particle content. Preferable, the plasma further comprises a stabilizing effective amount of at least one stabilizer, wherein prior to freeze-drying, said plasma and said at least one stabilizer or amino acid based buffer, which is added prior to freeze-drying. Preferably, the at least one stabilizer is one or more amino acids selected from the group consisting of glycine, glutamine, asparagine, taurine and combinations thereof. Preferably the amino acid based buffer is selected from the group consisting of N,N-Bis(2-hydroxyethyl)glycine, N,N-Bis(2-hydroxyethyl)taurine, glycineamide, and combinations thereof. Preferably, the plasma is subjected to high dose gamma irradiation and heat treatment as terminal sterilization methods.

Another embodiment of the invention is directed to methods for increasing coagulation factor stability of plasma in freeze-dried state, wherein said method comprises: treating the plasma by a hollow fiber filtration system to increase the total plasma protein concentration therein; and freeze-drying said treated plasma.

Another embodiment of the invention is directed to a composition comprising freeze-dried plasma having increased coagulation factor stability, wherein said freeze-dried plasma is glucose-free or has a reduced glucose content.

Another embodiment of the invention is directed to methods for increasing coagulation factor stability of freeze-dried plasma, wherein said method comprises: treating said plasma prior to freeze-drying to remove or reduce the glucose content therein; and freeze-drying said glucose-free or glucose-reduced plasma.

Another embodiment of the invention is directed to methods for increasing coagulation factor stability of freeze-dried plasma, wherein said method comprises collecting said plasma with glucose free anticoagulants; and freeze-drying said collected plasma.

Another embodiment of the invention is directed to a freeze-dried plasma of the invention, which is subjected to high dose gamma irradiation and heat treatment for terminal sterilization.

Another embodiment of the invention is directed top methods for rehydrating or reconstituting freeze-dried plasma, wherein said method provides for the control of gas content during said rehydration or reconstitution.

Another embodiment of the invention is directed to a hemostatic bandage or foam to control hemorrhage. Preferably, the hemostatic bandage or foam further comprises plasma containing an up-concentrated platelet particle content and an up-concentrated protein fraction co-freeze-dried with frozen thrombin and ice spheres.

Another embodiment of the invention comprises freeze-dried thrombin spheres where thrombin is stabilized with at least one stabilizer. Preferably, the stabilizer is selected from the group consisting of sucrose, trehalose, glycine, glutamine, arginine, glutamine dipeptides, glycine dipeptides, albumin, hydroxyethyl starch, and combinations thereof.

Other embodiments and technical advantages of the invention are set forth below and may be apparent from the drawings and the description of the invention, which follow, or may be learned from the practice of the invention.

DESCRIPTION OF THE INVENTION

Conventional compositions and method for the preservation of blood plasma involves freezing blood or plasma, transporting the frozen material and thawing the material under sterile conditions for subsequent use. This approach suffers from a number of shortcomings, especially when large amounts of plasma are needed or when refrigeration is not possible or practical. It has been surprisingly discovered that plasma can be preserved for storage and transportation at ambient temperatures with increased stability and at a physiological pH and osmolality. This invention is directed to plasma sources and the making of thereof, and freeze-dried plasma formats specifically designed for the trauma care field. Furthermore, the freeze-dried plasma products of the invention are stabilized against the damaging effects of high dose gamma irradiation and heat treatment and therefore can be produced and delivered in a sterilized form.

The following examples illustrate embodiments of the invention, but should not be viewed as limiting the scope of the invention.

EXAMPLES

Example 1

Plasma protein fraction was up-concentrated, glucose content was reduced, and stabilizing compositions of glutamine dipeptides, or combinations of glutamine dipeptides with glutamine, or glycine were added at the final concentrations indicated in Tables 2-10. Plasma was freeze-dried. The freeze-dried samples were subjected to a high dose gamma irradiation (50 kGy) and consequent heat treatment for 7 days at 45° C. Plasma coagulation properties, pH, osmolality, and residual moisture were determined as described in the text. Data are presented in Tables 2-10.

Example 2

Plasma was supplemented with Asparagine, Glutamine, Glycine, Bicine, or combinations of thereof, at the final concentrations indicated in Tables 12-14. Plasma was freeze-dried. The freeze-dried samples were subjected to heat treatment for 8 days at 40° C. Plasma coagulation properties, pH, osmolality, and residual moisture were determined as described in the text. Data are presented in Tables 12-14.

Example 3

Plasma was supplemented with 60 mM Glycine or a combination of 40 mM Glycine plus 20 mM GlycineAmide and freeze-dried. The freeze-dried samples were subjected to heat treatment for 4 days at 45° C. Plasma coagulation properties, pH, osmolality, and residual moisture were determined as described in the text. Data are presented in Tables 15-20. A combination of 40 mM Glycine plus 20 mM GlycineAmide (a total of 60 mM) shows increased capacity to stabilize freeze-dried plasma compared to 60 mM Glycine alone. Data are presented in Tables 15-20.

General Methodology
1. Plasma Sources: 1. Fresh frozen plasma (FFP) with up-concentrated protein fraction. 2. Platelet poor plasma (PPP) with up-concentrated platelet particle content.
3. PPP with up-concentrated platelet particle content and up-concentrated protein fraction.

Figure 1:
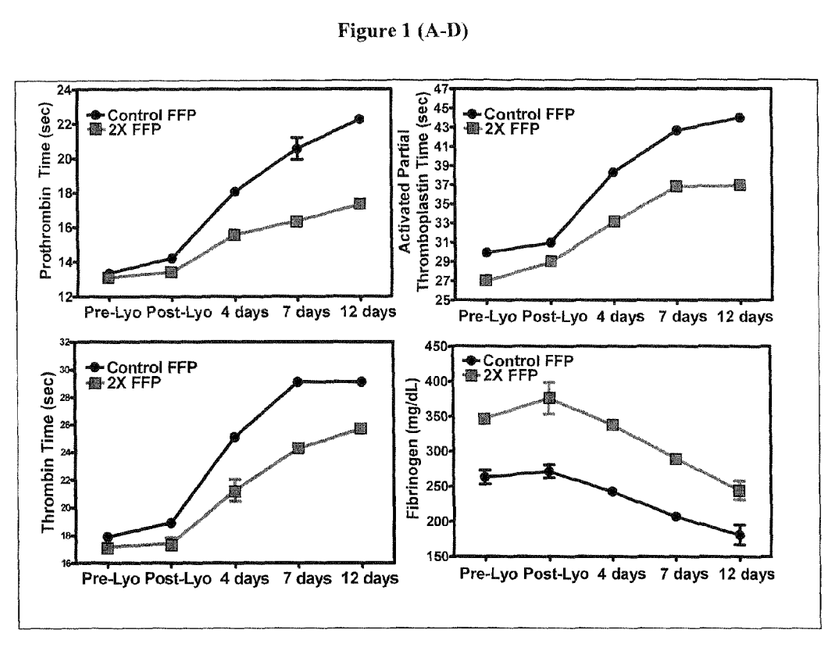
FIG. 1. Effect of plasma protein fraction up-concentration on stability of freeze-dried plasma. Plasma was circulated through a Spectrum Hollow Fiber Filtration System to produce plasma with up-concentrated protein fraction. Total protein concentration was 5.9 (g/dL) in control plasma and 9.7 (g/dL) in concentrated plasma. Control and Concentrated plasma were freeze-dried and subjected to heat treatment at 40° C. for 12 days. Prothrombin Time, Activated Partial Thromboplastin Time, Trombin Time and Fibrinogen were determined as described. Three independent experiments were performed. Mean values±S.D. are shown.

The three plasma sources are produced by circulating plasma through a Spectrum hollow fiber filtration system. Specifically, FFP with up-concentrated protein fraction is produced by circulating FFP through the filtration system, using a cartridge with a molecular cutoff≦100 kD. Control FFP and Concentrated FFP are freeze-dried and then subjected to forced degradation at 40° C. for 12 days. PT, APTT, TT (sec) and fibrinogen (mg/ml) were measured pre-lyophilization, post-lyophilization and at 4, 7, and 12 days of storage at 40° C. Data are presented in FIG. 1. The total protein concentration was 5.9 g/dL in control plasma and 9.7 g/dL in the concentrated plasma. Plasma clotting properties were measured as indicated in the text. Plasma clotting properties rapidly deteriorate in control plasma. In contrast, concentrated plasma displays increased stability in lyophilized form.

Platelet poor plasma (PPP) with up-concentrated platelet particle content fraction is produced by circulating PPP through the filtration system, using a cartridge with a molecular cutoff≦0.2 microns. PPP with up-concentrated platelet particle content and up-concentrated protein fraction is produced by circulating PPP through the filtration system, using a cartridge with a molecular cutoff≦0.2 microns and consequently a second cartridge with a molecular cutoff≦100 kD.

2. Freeze-Dried Plasma Formats for the Trauma Care Field
2.a. Freeze-Dried Plasma Supplemented with Stabilizers Beneficial for the Trauma Patient Stabilizers are specifically selected to exercise two functions: 1. Protect plasma proteins in lyophilized form and against gamma irradiation. 2. Contribute to the stabilization and survivability to the critically ill patient once plasma is liquefied and administered. This is a plasma product fortified with unique dipeptides, antioxidants, and free-radical scavengers. FFP was supplemented with specifically selected stabilizers, known for their beneficial effect on the trauma patient [18-27]. FFP was lyophilized and the stabilizers were evaluated for their ability to protect plasma in lyophilized form. The results of these experiments are summarized in Table 1. Glutamine-based dipeptides are not only excellent lyoprotectants for plasma proteins, outperforming every other compound tested, but surprisingly they are also the most beneficial supplements currently in use to help in the recovery of trauma patients. The glutamine dipeptides, Ala-Gln and Gly-Gln, have immunomodulatory, anabolic, gastrointestinal, and anti-oxidant activities and help patients recover from trauma, surgery, dehydration, and damage to the intestinal tract [17-21]. The Dipeptiven® injection, which is composed of the two glutamine dipeptides, Ala-Gln and Gly-Gin, is in clinical use to treat trauma patients. Therefore, the here described stabilization approach focuses on the Glutamine-based dipeptides as stabilizers for freeze-dried plasma produced for utilization in the trauma care field.

The Stabilization Approach—General.

Figure 2:
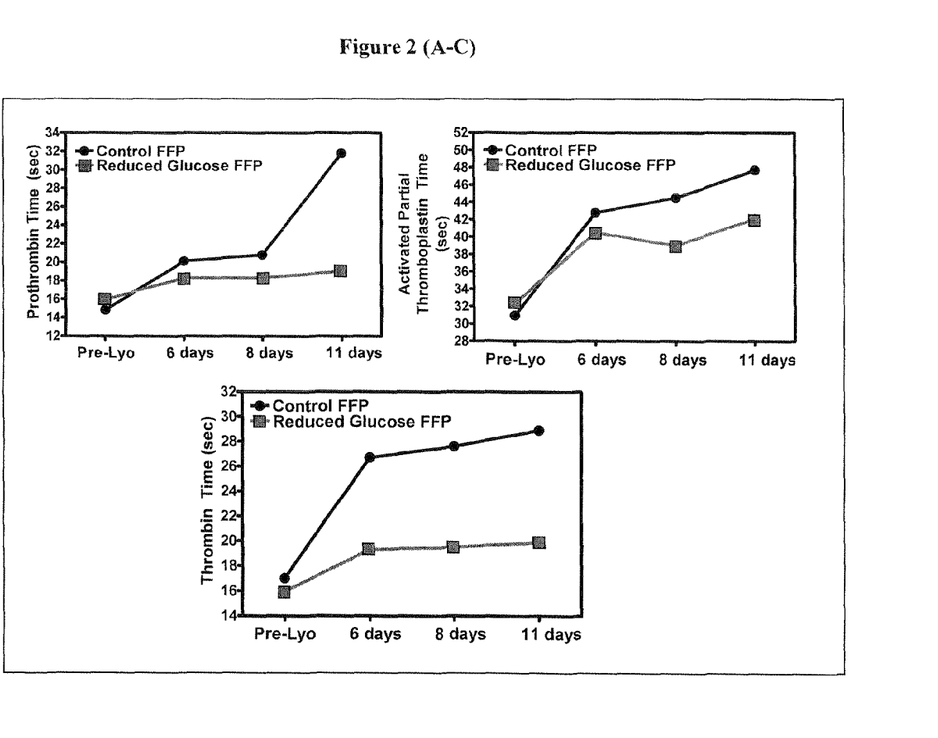
FIG. 2. Effect of glucose content reduction on stability of freeze-dried plasma. Plasma was circulated through a Spectrum Hollow Fiber Filtration System to produce plasma with reduced glucose concentration. Glucose concentration was 315 (mg/dL) in control plasma and 78 (mg/dL) in the reduced glucose plasma. Control and Reduced Glucose plasma were freeze-dried and subjected to heat treatment at 40° C. for 11 days. Prothrombin Time, Activated Partial Thromboplastins Time, Trombin Time were determined as described. Three independent experiments were performed. Mean values±S.D. are shown.

Glucose Removal. Glucose is a reducing sugar, a natural plasma constituent, and is also included in all anticoagulants used for plasma collection. It has been shown that Glucose participates in the Mailard reaction with proteins, which is extremely deleterious for proteins in lyo-state. Glucose removal using a hollow fiber filtration system or simple omission of glucose from the anticoagulant composition leads to an increase in coagulation factor stability in lyo-state. Data are presented in FIG. 2. Plasma glucose concentration was reduced using a spectrum hollow fiber filtration system. Glucose concentration was 315±18 (mg/dL) in control plasma and 78±18 (mg/dL) in the reduced glucose plasma. Control and reduced glucose plasma were lyophilized and subjected to heat treatment at 40° C. for 11 days. Plasma clotting properties were measured as indicated in the text. Plasma clotting properties rapidly deteriorate in control plasma. In contrast, plasma with reduced glucose content shows increased stability in lyophilized form. Protein Fraction Up-Concentration. Increasing the total plasma protein concentration by plasma processing via a hollow fiber filtration system leads to an increase in coagulation factor stability in lyo-state (FIG. 1), and provides for a standardized product.

Glutamine-based amino acids/dipeptides formulation. GlyGln, AlaGln and glutamine are added at predetermined concentrations to whole plasma prior to lyophilization.

The three stabilization approaches, glucose removal, protein up-concentration, and supplementation with glutamine-based dipeptides, are three protein specific stabilization technologies. Pathogens are not proteins. They are polynucleotides. Polynucleotides are more sensitive to gamma irradiation than proteins. The lead hypothesis of this work is that a combination of the here described three protein specific approaches will be an effective method for plasma protein stabilization in lyophilized state as well as plasma protein stabilization against the damaging effects of high dose gamma irradiation and heat treatment. FFP was subjected to a glucose reduction step, a protein up-concentration step and supplementation with glutamine-based dipeptides. The stabilized plasma was then lyophilized. The stabilized lyophilized plasma and control non-treated lyophilized plasma were subjected to gamma irradiation (50 kGy), on ice, and subsequent heat treatment at 45° C. for 7 days. Data presented in Tables 2-10 show that the clotting properties of stabilized lyophilized plasma and pH are fully protected against the damaging effects of a dual application of gamma irradiation and heat treatment. In contrast, plasma clotting properties are substantially deteriorated in control lyophilized plasma and display values, which are outside the normal range.

The Stabilization Approach—pH Stabilization

Citric acid and ascorbic acid were found to be suitable pH adjusters for freeze-dried plasma. However, they do not have any significant stabilizing effect on plasma proteins. Therefore, pH adjusters have to be paired with stabilizers [10].

A variety of biological buffers were tested for their ability to stabilize pH in lyophilized plasma. Results varied significantly. Amino acid—based buffers showed the highest ability to preserve plasma pH in freeze-dried state. They were found not only to stabilize pH, but also showed a strong stabilizing effect per se on plasma proteins in freeze-dried state. Buffers containing glycine or taurine in their structures were very effective. Examples: bicine, glycinamide, N,N-Bis(2-hydroxyethyl)taurine.

Table 1 shows the ability of selected compounds beneficial to trauma patients to act as lyoprotectants for plasma. Plasma supplemented with the listed compounds was lyophilized, and subjected to heat treatment at 40° C. for 4 days. Here, the compounds are given only a qualitative description, based on their relative ability to protect plasma clotting properties.

2b. A Taurine—Stabilized, lyophilized platelet poor plasma with up-concentrated platelet particle content. PPP with up-concentrated particle content displays platelet like properties as evidenced by thrombelastography measurements. Maximum amplitude (mm) was measured using a Computerized Thrombelastograph. PPP with up-concentrated platelet particle content and supplemented with taurine and bicine displays platelet like properties that are well preserved in freeze-dried state. The results of these experiments are presented in Table 11.

It is noted that taurine is a unique antioxidant and very beneficial amino acid, which is given as a supplement to trauma patients [22-24]. Hypotaurinemia is a state, which develops in trauma, sepsis and critical illness patients.

2c. A Bicarbonate-enriched, $CO_2$-free lyophilized plasma: Supports the acidosis patient. Sodium bicarbonate injection is indicated in the treatment of metabolic acidosis; It may lead to hypernatremia. Plasma with elevated bicarbonate concentration is produced without causing an increase in the normal plasma sodium concentration. Experimental: FFP is mixed with injectable grade water in the ratio of 1 vol:0.25 vol. The latter reduces the original $Na^+$ approximately by 30 mEq. The original Bicarbonate content is reduced by approx. 6 mEq. FFP protein fraction is then up-concentrated using a 100 kD cartridge. FFP is lyophilized and co-packaged with 30 mEq NaBicarbonate. On reconstitution FFP contains: the original, physiological Na+ concentration, while the bicarbonate concentration has increased by approx. 24 mEq.

2d. A Rehydration medium with controlled-gas content: The gas content of the rehydration medium for freeze-dried plasma, can be controlled. The water to be used for reconstitution can be supplemented with any gas, at any desirable concentration, which is considered beneficial for the trauma patient. Thus, the freeze-dry plasma can be reconstituted, and thereby supplemented with any gas of choice. Zuckerbraun et al. have demonstrated that the administration of exogenoius carbon monoxide (CO) at low concentration provides cytoprotection in vivo and in vitro [28].

An oxygen-free rehydration medium can be prepared utilizing standard degassing methods for water. The latter assures the preparation of an anoxic plasma product on reconstitution that will alleviate ischemia reperfusion injury.

Figure 3:
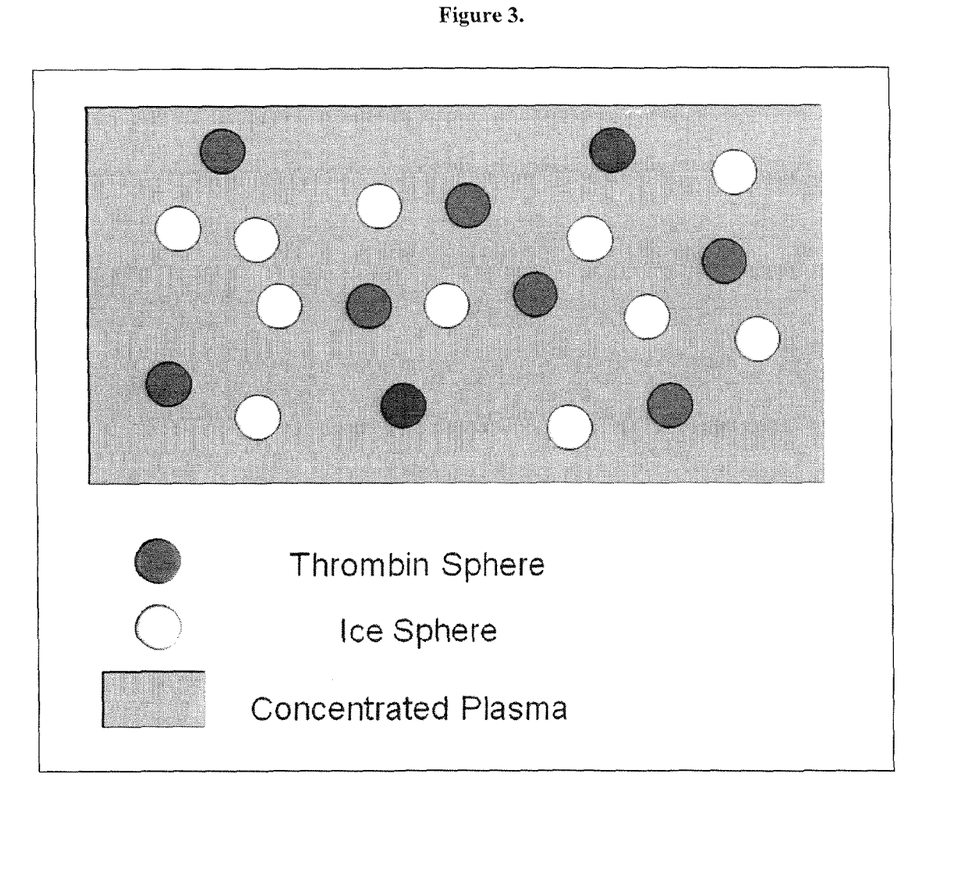
FIG. 3. Freeze-dried plasma composition showing thrombin spheres and ice spheres according to one embodiment of the invention.

2e. A novel hemostatic bandage construct: Platelet Poor Plasma (PPP) with up-concentrated platelet particle content and up-concentrated protein fraction is co-lyophilized with frozen thrombin and ice spheres (FIG. 3).

Plasma Supply

Fresh donor plasma (FDP) units were obtained from The Walter Reed Army Medical Center under a protocol approved by the Institutional Review Board (200 ml plasma containing approximately 36 ml of ACD-A anticoagulant). The plasma units were stored frozen at −80° C. and used within 3 months of donation. At the time of the experiments, five plasma units, from five different donors, were rapidly thawed at 37 C in a plasma thawer, pooled together under sterile conditions and processed immediately as a pooled plasma product.

Reagents

Glutamine, asparagine, glycine, taurine, 1-carnosine, Gly-Gln, Ala-Gln, histidine, aminoguanidine, ubiquitin, citric acid, trimethylglycine, arginine, and beta-hydroxybutirate, were purchased from Sigma (St. Louis, Mo., USA). The reagents required to perform prothrombin time (PT), activated partial thromboplastin time (APTT), thrombin time (TT) and fibrinogen, including controls and calibrators were obtained from Diagnostica Stago (Parsippany, N.J., USA).

Experimental Design

Plasma was subjected to three different stabilization approaches or a combination thereof and lyophilized. These stabilization approaches included, reduction of plasma glucose content using a spectrum hollow fiber filtration system, up-concentration of plasma protein fraction using the same filtration system, and direct addition of stabilizers to plasma at specified final concentrations. Stabilized lyophilized plasma and control lyophilized plasma were subjected to heat treatment at 40° C. or at 45 C for up to 12 days in a former scientific incubator. In selected experiments, the freeze-dried samples were subjected to gamma irradiation (50 kGy), on ice, and subsequent heat treatment as indicated in the figure legends.

Freeze-Drying

Freeze-drying was performed on a mid-scale TelStar lyophilizer (LyoBeta25, Terrassa, Spain). Five-milliliter aliquots of plasma were transferred to plastic SCHOTT TopPac vials (Schott North America, Lebanon, Pa.), which were placed on the shelf of the lyophilizer at room temperature. Samples were frozen to minus 40° C. at a rate of 1 C/min. Primary drying was carried out at minus 30° C. Secondary drying was carried out at 30° C. After secondary drying completion, the vials were sealed with rubber stoppers (Dalkyo Fluorotec, West Pharmaceutical Sciences) under nitrogen gas inside the chamber.

Rehydration

The amount of water necessary for reconstitution was determined as follows: the liquid plasma, pre-lyophilized (5 ml plasma/bottle) and the post-lyophilized plasma were weighed using a Mettler-Toledo balance A6104 and then averaged. The mean weight difference between the two indicated the amount of water needed for rehydration. Weight determination was performed on 56 bottles. Freeze-dried plasma was rehydrated using 4.7 ml of ultra pure reagent grade water (NERL Diagnostics) per bottle.

Coagulation Assays In Vitro

An automated coagulation instrument, the STA-R (Diagnostica Stago, Parsippany, N.J.), was used for in vitro testing of the coagulation system. Prothrombin time (PT), activated partial thromboplastin time (APTT) and thrombin time (TT) were calculated in seconds, fibrinogen was measured in mg/dl, and factors V, VII, VIII, IX and X percentage activity were determined according to standard procedures developed by Diagnostica Stago. Percentage activity of protein C, protein S and antithrombin III were also measured. Low and high limits were set by the corresponding controls for each test. All tests were carried out at 37° C.

$Na^+$, $K^+$, $Cl^-$ Concentration, $pCO_2$ and pH

The above plasma chemical characteristics were measured using a Corning 855 clinical blood gas analyzer (Ciba-Corning Diagnostica, Medfield, Mass.). The Corning 855 uses ion selective electrodes to determine $pCO_2$, pH, $Na^+$, $K^4$ and $Cl^-$ levels in plasma. All reagents and supplies are available from Bayer Diagnostics. All tests were performed according to the standard operating procedure.

Total Protein, Phosphates and Glucose Concentration

Total protein, phosphates and glucose concentration in plasma were determined using an ACE clinical chemistry analyzer (Alfa Wasserman, West Caldwell, N.J.). Sample processing was performed according to the manufacturer's standard operating procedures as detailed in the Alfa Wassermann ACE System Users Guide and the product inserts for the assays. All reagents and supplies are available from Alfa Wassermann.

Osmolality

Osmolality was determined by freezing point depression using an Advanced Instruments Model 3900 Osmometer (Norwood, Mass.). Results are defined as the osmoles of solute particles per kilogram of pure solvent and expressed as mosM/kg.

Thrombelastography

Thrombelastography was carried out using a Computerized Thrombelastograph (5000 (Haemoscope) pre-warmed to 37° C. A thrombin assay was performed using thrombin (0.6 U/ml final concentration) and CaCl2 (6.25 mM final concentration). The parameter measured was the maximum amplitude (MA), which defines the maximum shear modulus or strength of the fibrin strands including the contribution of platelets.

Moisture Determination

Residual moisture in the freeze-dried cakes was determined using a Computrac Vapor Pro Rx moisture analyzer (Arizona Instrument, Tempe Ariz.). Residual moisture was below 1% in all freeze-dried samples.

TABLE 1

Ability of selected compounds beneficial for trauma patients to act as lyoprotectants for whole plasma.

| No Effect | Average Protectant | Strong Protectant | Excellent Protectant |
|---|---|---|---|
| Citric Acid | Ubiquitin | Glutamine | Gly-Gln |
| TrimethylGlycine | Aminoguanidine | Glycine | Ala-Gln |
| Arginine | Histidine | Taurine | |
| BetaHydroxybutirate | | L-Carnosine | |

A qualitative description is assigned to each compound.

TABLE 2

Stabilizing Effect of glucose removal, protein up-concentration, and addition of glutamine dipeptides, glutamine, and glycine on plasma Prothrombin Time.

| | Prothrombin Time (sec) | | |
|---|---|---|---|
| | Pre-Lyo | Post-Lyo | +Gamma Irradiation (50 kGy) + 7 days at 45° C. |
| Control Plasma | 14.1 ± 0.15 | 14.9 ± 0.03 | 23.9 ± 0.09 |
| +15 mM GlyGln + 15 mM AlaGln | 13.2 ± 0.28 | 13.1 ± 0.15 | 14.0 ± 0.08 |
| +15 mM GlyGln + 15 mM AlaGln + 30 mM Gln | 13.1 ± 0.67 | 13.5 ± 0.17 | 13.6 ± 0.11 |
| +15 mM GlyGln + 15 mM AlaGln + 30 mM Gln + 15 mM Gly | 13.2 ± 0.03 | 13.0 ± 0.06 | 13.5 ± 0.03 |

Plasma was stabilized, freeze-dried, and subjected to gamma irradiation and heat treatment as described in the text. Three independent experiments were performed. Mean values ± S.D. are shown.

TABLE 3

Stabilizing Effect of glucose removal, protein up-concentration, and addition of glutamine dipeptides, glutamine, and glycine on plasma Activated Partial Thromboplastin Time.

| | Activated Partial Thromboplastin Time (sec) | | |
|---|---|---|---|
| | Pre-Lyo | Post-Lyo | +Gamma Irradiation (50 kGy) + 7 days at 45° C. |
| Control Plasma | 26.2 ± 0.17 | 28.0 ± 0.07 | 46.5 ± 0.3 |
| +15 mM GlyGln + 15 mM AlaGln | 26.8 ± 0.05 | 28.0 ± 0.46 | 31.0 ± 0.23 |
| +15 mM GlyGln + 15 mM AlaGln + 30 mM Gln | 27.2 ± 0.14 | 28.2 ± 0.10 | 29.0 ± 0.44 |
| +15 mM GlyGln + 15 mM AlaGln + 30 mM Gln + 15 mM Gly | 26.9 ± 0.08 | 27.8 ± 0.20 | 28.7 ± 0.20 |

Plasma was stabilized, freeze-dried, and subjected to gamma irradiation and heat treatment as described in the text. Three independent experiments were performed. Mean values ± S.D. are shown.

TABLE 4

Stabilizing Effect of glucose removal, protein up-concentration, and addition of glutamine dipeptides, glutamine, and glycine on plasma Thrombin Time.

| | Thrombin Time (sec) | | |
|---|---|---|---|
| | Pre-Lyo | Post-Lyo | +Gamma Irradiation (50 kGy) + 7 days at 45° C. |
| Control Plasma | 17.6 ± 0.08 | 18.1 ± 0.48 | 24.8 ± 0.17 |
| +15 mM GlyGln + 15 mM AlaGln | 16.8 ± 0.08 | 16.4 ± 0.11 | 18.2 ± 0.12 |
| +15 mM GlyGln + 15 mM AlaGln + 30 mM Gln | 17.5 ± 0.06 | 16.2 ± 0.08 | 16.9 ± 0.41 |
| +15 mM GlyGln + 15 mM AlaGln + 30 mM Gln + 15 mM Gly | 17.6 ± 0.03 | 16.5 ± 0.2 | 17.1 ± 0.06 |

Plasma was stabilized, freeze-dried, and subjected to gamma irradiation and heat treatment as described in the text. Three independent experiments were performed. Mean values ± S.D. are shown.

TABLE 5

Stabilizing Effect of glucose removal, protein up-concentration, and addition of glutamine dipeptides, glutamine, and glycine on plasma Factor V Activity (%).

| | Factor V Activity (%) | | |
|---|---|---|---|
| | Pre-Lyo | Post-Lyo | +Gamma Irradiation (50 kGy) + 7 days at 45° C. |
| Control Plasma | 88 ± 2.7 | 60 ± 0.66 | 18 ± 0.33 |
| +15 mM GlyGln + 15 mM AlaGln | 117 ± 2.33 | 93 ± 3.0 | 90 ± 2.6 |
| +15 mM GlyGln + 15 mM AlaGln + 30 mM Gln | 118 ± 4.41 | 92 ± 3.75 | 98 ± 5.5 |
| +15 mM GlyGln + 15 mM AlaGln + 30 mM Gln + 15 mM Gly | 95 ± 13.0 | 94 ± 2.0 | 99 ± 5.6 |

Plasma was stabilized, freeze-dried, and subjected to gamma irradiation and heat treatment as described in the text. Three independent experiments were performed. Mean values ± S.D. are shown.

TABLE 6

Stabilizing Effect of glucose removal, protein up-concentration, and addition of glutamine dipeptides, glutamine, and glycine on plasma Factor X Activity (%).

| | Factor X Activity (%) | | |
|---|---|---|---|
| | Pre-Lyo | Post-Lyo | +Gamma Irradiation (50 kGy) + 7 days at 45° C. |
| Control Plasma | 75 ± 8.7 | 171 ± 3.1 | 50 ± 0.66 |
| +15 mM GlyGln + 15 mM AlaGln | 148 ± 1.2 | 143 ± 4.5 | 95 ± 2.0 |
| Concentrated + 15 mM GlyGln + 15 mM AlaGln + 30 mM Gln | 146 ± 3.2 | 139 ± 0.66 | 104 ± 1.2 |
| Concentrated + 15 mM GlyGln + 15 mM AlaGln + 30 mM Gln + 15 mM Gly | 148 ± 2.7 | 178 ± 3.2 | 106 ± 1.4 |

Plasma was stabilized, freeze-dried, and subjected to gamma irradiation and heat treatment as described in the text. Three independent experiments were performed. Mean values ± S.D. are shown.

TABLE 7

Stabilizing Effect of glucose removal, protein up-concentration, and addition of glutamine dipeptides, glutamine, and glycine on plasma Fibrinogen (mg/dL).

| | Fibrinogen (mg/dL) | | |
|---|---|---|---|
| | Pre-Lyo | Post-Lyo | +Gamma Irradiation (50 kGy) + 7 days at 45° C. |
| Control Plasma | 224 ± 14.6 | 251 ± 2.3 | 137 ± 7.3 |
| +15 mM GlyGln + 15 mM AlaGln | 341 ± 2.08 | 341 ± 3.0 | 293 ± 12.6 |
| +15 mM GlyGln + 15 mM AlaGln + 30 mM Gln | 349 ± 3.7 | 328 ± 8.1 | 336 ± 1.1 |
| +15 mM GlyGln + 15 mM AlaGln + 30 mM Gln + 15 mM Gly | 349 ± 3.3 | 331 ± 2.9 | 336 ± 3.0 |

Plasma was stabilized, freeze-dried, and subjected to gamma irradiation and heat treatment as described in the text. Three independent experiments were performed. Mean values ± S.D. are shown.

TABLE 8

Stabilizing Effect of glucose removal, protein up-concentration, and addition of glutamine dipeptides, glutamine, and glycine on plasma Total Protein (g/dL).

| | Total Protein (g/dL) | | |
|---|---|---|---|
| | Pre-Lyo | Post-Lyo | +Gamma Irradiation (50 kGy) + 7 days at 45° C. |
| Control Plasma | 5.9 ± 0.0 | 5.9 ± 0.0 | 5.9 ± 0.0 |
| +15 mM GlyGln + 15 mM AlaGln | 9.4 ± 0.0 | 9.1 ± 0.0 | 9.3 ± 0.1 |
| +15 mM GlyGln + 15 mM AlaGln + 30 mM Gln | 9.7 ± 0.0 | 8.8 ± 0.0 | 9.0 ± 0.0 |
| +15 mM GlyGln + 15 mM AlaGln + 30 mM Gln + 15 mM Gly | 9.6 ± 0.0 | 8.8 ± 0.0 | 9.1 ± 0.0 |

Plasma was stabilized, freeze-dried, and subjected to gamma irradiation and heat treatment as described in the text. Three independent experiments were performed. Mean values ± S.D. are shown.

TABLE 9

Stabilizing Effect of glucose removal, protein up-concentration, and addition of glutamine dipeptides, glutamine, and glycine on plasma pH.

| | pH | | |
|---|---|---|---|
| | Pre-Lyo | Post-Lyo | +Gamma Irradiation (50 kGy) + 7 days at 45° C. |
| Control Plasma | 7.139 ± 0.0 | Out of range | Out of range |
| +15 mM GlyGln + 15 mM AlaGln | 7.247 ± 0.0 | 7.442 ± 0.0 | 7.394 ± 0.0 |
| +15 mM GlyGln + 15 mM AlaGln + 30 mM Gln | 7.166 ± 0.0 | 7.370 ± 0.0 | 7.324 ± 0.0 |
| +15 mM GlyGln + 15 mM AlaGln + 30 mM Gln + 15 mM Gly | 7.222 ± 0.0 | 7.383 ± 0.0 | 7.372 ± 0.0 |

Plasma was stabilized, freeze-dried, and subjected to gamma irradiation and heat treatment as described in the text. Three independent experiments were performed. Mean values ± S.D. are shown.

TABLE 10

Stabilizing Effect of glucose removal, protein up-concentration, and addition of glutamine dipeptides, glutamine, and glycine on plasma Osmolality.

| | Osmolality (mOsmM) | |
|---|---|---|
| | Pre-Lyo | +Gamma Irradiation (50 kGy) + 7 days at 45° C. |
| Control Plasma | 278 ± 1.1 | 274 ± 1.1 |
| +15 mM GlyGln + 15 mM AlaGln | 289 ± 0.3 | 287 ± 0.0 |
| +15 mM GlyGln + 15 mM AlaGln + 30 mM Gln | 324 ± 1.2 | 322 ± 0.0 |
| +15 mM GlyGln + 15 mM AlaGln + 30 mM Gln + 15 mM Gly | 329 ± 0.5 | 331 ± 0.3 |

Plasma was stabilized, freeze-dried, and subjected to gamma irradiation and heat treatment as described in the text. Three independent experiments were performed. Mean values ± S.D. are shown.

TABLE 11

Stabilizing Effect of Taurine and Bicine on Platelet Poor Plasma (PPP) with up-concentrated platelet particle content.

| | Maximum Amplitude (mm) | | |
|---|---|---|---|
| | Pre-Lyo | Post-Lyo | 3 days at 40° C. |
| Control PPP | 26.2 | 22.1 | 12.1 |
| Concentrated PPP | 49.7 | 40.5 | 14.3 |
| Concentrated PPP + 60 mM Taurine + 2 mM Bicine | 46.2 | 46.7 | 41.7 |

PPP was freeze-dried and subjected to heat treatment for 3 days at 40° C. The Maximum Amplitude was measured using a Computerized Thrombelastograph as descript in the text. Three independent experiments were performed. Mean values are shown.

TABLE 12

Stabilizing Effect of asparagine, bicine, glutamine, and glycine on plasma Prothrombine Time.

| | Prothrombin Time (sec) | | | |
|---|---|---|---|---|
| | Pre-Lyo | Post-Lyo | 6 days at 40° C. | 8 days at 40° C. |
| Control FFP | 14.1 ± 0.3 | 14.7 ± 0.1 | 17.7 ± 0.5 | 18.0 ± 0.5 |
| +60 mM Asparagine | 13.9 ± 0.3 | 14.2 ± 0.3 | 15.3 ± 0.2 | 16.0 ± 0.3 |
| +60 mM Asparagine + 2.5 mg/ml Bicine | 14.5 ± 0.1 | 14.6 ± 0.2 | 15.2 ± 0.2 | 15.3 ± 0.1 |
| +60 mM Glutamine | 13.8 ± 0.2 | 14.4 ± 0.5 | 15.1 ± 0.1 | 15.6 ± 0.2 |
| +60 mM Glutamine + 2.5 mg/ml Bicine | 14.1 ± 0.4 | 14.4 ± 0.1 | 14.9 ± 0.2 | 15.0 ± 0.4 |
| +60 mM Glycine | 13.8 ± 0.5 | 14.3 ± 0.2 | 15.4 ± 0.3 | 15.6 ± 0.1 |
| +60 mM Glycine + 2.5 mg/ml Bicine | 14.1 ± 0.2 | 14.4 ± 0.1 | 14.9 ± 0.4 | 15.2 ± 0.2 |
| +30 mM Asparagine + 30 mM Glycine | 13.9 ± 01 | 14.5 ± 02 | 15.0 ± 0.3 | 15.1 ± 0.1 |
| +30 mM Glutamine + 30 mM Glycine | 14.0 ± 0.4 | 14.4 ± 0.3 | 15.0 ± 03 | 15.2 ± 0.2 |

Plasma was stabilized, freeze-dried, and subjected to heat treatment as described in the text. Three independent experiments were performed. Mean values ± S.D. are shown.

TABLE 13

Stabilizing Effect of asparagine, bicine, glutamine, and glycine on plasma Activated Partial Thromboplastine Time.

| | Activated Partial Thromboplastin Time (sec) | | | |
|---|---|---|---|---|
| | Pre-Lyo | Post-Lyo | 6 days at 40° C. | 8 days at 40° C. |
| Control FFP | 29.0 ± 0.2 | 30.3 ± 0.4 | 37.0 ± 0.3 | 37.9 ± 0.4 |
| +60 mM Asparagine | 30.0 ± 0.1 | 30.7 ± 0.1 | 33.0 ± 0.2 | 34.4 ± 0.3 |
| +60 mM Asparagine + 2.5 mg/ml Bicine | 30.2 ± 0.3 | 31.1 ± 0.1 | 32.6 ± 0.3 | 33.4 ± 0.2 |
| +60 mM Glutamine | 29.6 ± 0.4 | 30.7 ± 0.2 | 32.4 ± 0.5 | 33.4 ± 0.1 |
| +60 mM Glutamine + 2.5 mg/ml Bicine | 30.3 ± 0.1 | 31.1 ± 0.4 | 32.8 ± 0.4 | 33.0 ± 0.2 |
| +60 mM Glycine | 28.7 ± 0.3 | 29.9 ± 0.3 | 32.6 ± 0.3 | 33.6 ± 0.2 |
| +60 mM Glycine + 2.5 mg/ml Bicine | 29.2 ± 0.1 | 29.9 ± 0.5 | 32.0 ± 0.1 | 32.2 ± 0.2 |
| +30 mM Asparagine + 30 mM Glycine | 29.4 ± 0.1 | 29.9 ± 0.2 | 32.4 ± 0.2 | 32.8 ± 0.3 |
| +30 mM Glutamine + 30 mM Glycine | 29.1 ± 0.2 | 30.7 ± 0.3 | 32.5 ± 0.3 | 32.7 ± 0.2 |

Plasma was stabilized, freeze-dried, and subjected to heat treatment as described in the text. Three independent experiments were performed. Mean values ± S.D. are shown.

TABLE 14

Stabilizing Effect of asparagine, bicine, glutamine, and glycine on plasma Thrombine Time.

| | Thrombin Time (sec) | | | |
|---|---|---|---|---|
| | Pre-Lyo | Post-Lyo | 6 days at 40° C. | 8 days at 40° C. |
| Control FFP | 17.9 ± 0.02 | 19.4 ± 0.03 | 24.2 ± 0.04 | 25.9 ± 0.02 |
| +60 mM Asparagine | 18.6 ± 0.03 | 18.6 ± 0.08 | 19.5 ± 0.02 | 20.5 ± 0.05 |
| +60 mM Asparagine + 2.5 mg/ml Bicine | 19.0 ± 0.06 | 18.8 ± 0.02 | 19.9 ± 0.02 | 19.8 ± 0.04 |
| +60 mM Glutamine | 19.2 ± 0.05 | 19.3 ± 0.06 | 20.7 ± 0.02 | 21.3 ± 0.01 |
| +60 mM Glutamine + 2.5 mg/ml Bicine | 19.6 ± 0.03 | 19.4 ± 0.05 | 20.1 ± 0.06 | 20.6 ± 0.03 |
| +60 mM Glycine | 18.1 ± 0.04 | 18.8 ± 0.02 | 19.9 ± 0.02 | 19.7 ± 0.02 |
| +60 mM Glycine + 2.5 mg/ml Bicine | 18.2 ± 0.04 | 18.4 ± 0.08 | 19.2 ± 0.05 | 19.6 ± 0.06 |
| +30 mM Asparagine + 30 mM Glycine | 18.4 ± 0.05 | 18.7 ± 0.06 | 19.4 ± 0.07 | 19.8 ± 0.02 |
| +30 mM Glutamine + 30 mM Glycine | 18.2 ± 0.02 | 18.6 ± 0.07 | 19.5 ± 0.02 | 20.2 ± 0.04 |

Plasma was stabilized, freeze-dried, and subjected to heat treatment as described in the text. Three independent experiments were performed. Mean values ± S.D. are shown.

TABLE 15

Stabilizing Effect of glycine and glycineamide on plasma Prothrombine Time.

| | Prothrombine Time (sec) | | |
|---|---|---|---|
| | Pre-Lyo | Post-Lyo | 4 days at 45° C. |
| Control | 14.3 ± 0.2 | 14.5 ± 0.1 | 18.8 ± 0.03 |
| 60 mM Glycine | 14.1 ± 0.9 | 14.4 ± 0.1 | 15.6 ± 0.1 |
| 40 mM Glycine + 20 mM GlycineAmide | 14.6 ± 0.6 | 14.5 ± 0.03 | 15.0 ± 0.1 |

Plasma was stabilized, freeze-dried, and subjected to heat treatment as described in the text. Three independent experiments were performed. Mean values ± S.D. are shown.

TABLE 16

Stabilizing Effect of glycine and glycineamide on plasma Activated Partial Thromboplastine Time.

| | Activated Partial Thromboplastin Time (sec) | | |
|---|---|---|---|
| | Pre-Lyo | Post-Lyo | 4 days at 45° C. |
| Control | 27.1 ± 0.2 | 29.3 ± 0.3 | 33.1 ± 0.5 |
| 60 mM Glycine | 26.3 ± 0.9 | 28.3 ± 0.7 | 29.9 ± 0.4 |
| 40 mM Glycine + 20 mM GlycineAmide | 24.9 ± 0.7 | 26.3 ± 0.02 | 28.0 ± 0.1 |

Plasma was stabilized, freeze-dried, and subjected to heat treatment as described in the text. Three independent experiments were performed. Mean values ± S.D. are shown.

TABLE 17

Stabilizing Effect of glycine and glycineamide on plasma Thrombine Time.

| | Thrombin Time (sec) | | |
|---|---|---|---|
| | Pre-Lyo | Post-Lyo | 4 days at 45° C. |
| Control | 17.8 ± 0.03 | 18.8 ± 0.2 | 26.3 ± 0.07 |
| 60 mM Glycine | 17.5 ± 0.08 | 18.3 ± 0.06 | 20.1 ± 0.3 |
| 40 mM Glycine + 20 mM GlycineAmide | 19.0 ± 0.06 | 18.9 ± 0.16 | 19.7 ± 0.12 |

Plasma was stabilized, freeze-dried, and subjected to heat treatment as described in the text. Three independent experiments were performed. Mean values ± S.D. are shown.

TABLE 18

Stabilizing Effect of glycine and glycineamide on plasma Factor V Activity (%).

| | Factor V Activity (%) | | |
|---|---|---|---|
| | Pre-Lyo | Post-Lyo | 4 days at 45° C. |
| Control | 74 ± 0.9 | 72 ± 3.6 | 28 ± 2.2 |
| 60 mM Glycine | 75 ± 0.9 | 74 ± 0.8 | 51 ± 4.2 |
| 40 mM Glycine + 20 mM GlycineAmide | 76 ± 0.6 | 68 ± 0.8 | 68 ± 0.3 |

Plasma was stabilized, freeze-dried, and subjected to heat treatment as described in the text. Three independent experiments were performed. Mean values ± S.D. are shown.

TABLE 19

Stabilizing Effect of glycine and glycineamide on plasma Factor VIII Activity (%).

| | Factor VIII Activity (%) | | |
|---|---|---|---|
| | Pre-Lyo | Post-Lyo | 4 days at 45° C. |
| Control | 115 ± 6.0 | 81 ± 4.9 | 45 ± 1.8 |
| 60 mM Glycine | 195 ± 3.6 | 97 ± 4.9 | 75 ± 4.2 |
| 40 mM Glycine + 20 mM GlycineAmide | 160 ± 2.7 | 104 ± 2.1 | 93 ± 1.8 |

Plasma was stabilized, freeze-dried, and subjected to heat treatment as described in the text. Three independent experiments were performed. Mean values ± S.D. are shown.

TABLE 20

Stabilizing Effect of glycine and glycineamide on plasma pH.

| | pH | | |
|---|---|---|---|
| | Pre-Lyo | Post-Lyo | 4 days at 45° C. |
| Control | 7.122 ± 0.00 | Out of range | Out of range |
| 60 mM Glycine | 7.25 ± 5.2 | 7.88 ± 0.00 | 7.86 ± 0.00 |
| 40 mM Glycine + 20 mM GlycineAmide | 6.9 ± 0.0 | 7.4 ± 0.0 | 7.3 ± 0.0 |

Plasma was stabilized, freeze-dried, and subjected to heat treatment as described in the text. Three independent experiments were performed. Mean values ± S.D. are shown.

Other embodiments and uses of the invention will be apparent to those skilled in the art from consideration of the specification and practice of the invention disclosed herein. All references cited herein, including all patents and publications that are cited for any reason, including U.S. Provisional Application No. 60/998,928, on which priority is based, are specifically and entirely incorporated by reference. Furthermore, the term "comprising" includes the terms "consisting of" and "consisting essentially of." The specification and examples should be considered exemplary only with the true scope and spirit of the invention embodied within the following claims.

REFERENCES

[1] Krutvacho, T. Chuansumrit, A. Isarangkura, P. Pintadit, P. Hathirat, P. and Chiewsilp, P. Response of hemophilia with bleeding to fresh dry plasma, *Southeast Asian J Trop Med Public Health* 24 (1993), pp. 169-173.
[2] Chuansumrit, A. Krasaesub, S. Angchaisuksiri, P. Hathirat, P. and Isarangkura, P. Survival analysis of patients with haemophilia at the International Haemophilia Training Centre, Bangkok, Thailand, *Haemophilia* 10 (2004), pp. 542-549.
[3] Committee on Plasma and Plasma Substitutes of the Division of Medical Sciences, National Research Council, Statement on normal (whole, pooled) human plasma, *Transfusion* 8 (1968), pp. 57-59.
[4] Horowitz, B. Bonomo, R. Prince, A. Chin, S. Brotman, B. and Shulman, R. Solvent/detergent-treated plasma: a virus-inactivated substitute for fresh frozen plasma, *Blood* 79 (1992), pp. 826-831.
[5] Goodrich, R. The use of riboflavin for the inactivation of pathogens in blood products, *Vox Sang* 78 (2000), pp. 211-215.
[6] Wollowitz, S. Fundamentals of the psoralen-based Helinx technology for inactivation of infectious pathogens and leukocytes in platelets and plasma, *Semin Hematol* 38 (2001), pp. 4-11.
[7] Hellstern, P. Sachse, H. Schwinn, H. and Oberfrank, K. Manufacture and in vitro characterization of a solvent/detergent-treated human plasma, *Vox Sang* 63 (1992), pp. 178-185.
[8] Trobisch, H. Results of a quality-control study of lyophilized pooled plasmas which have been virally inactivated using a solvent detergent method (modified Horowitz procedure), *Beitr Infusionsther* 28 (1991), pp. 92-109.
[9] Hugler, P. Trobish, H. Neuman, H. Moller, Sirtl, C. and Derdak M. Quality control of three different conventional fresh-frozen plasma preparations and one new virus-inactivated lyophilized pooled plasma preparation, *Klin Wochenschr* 69 (1991), pp. 157-161.
[10] Bakaltcheva, I. O'Sullivan, A. M. Hmel, P. Ogbu, H. Freeze-dried whole plasma: Evaluating sucrose, trehalose, sorbitol, mannitol and glycine as stabilizers. *Thromb Res.* 120 (2007), pp. 105-16.
[11] Zbikowska, H. Nowak, P. Wachowicz, B. Protein modification caused high dose gamma irradiation in cryo-sterilized plasma: protective effects of ascorbate. *Free Radic Biol Med* 40 (2006), pp. 536-42.
[12] Zbikowska, H. Nowak, P. Wachowicz, B. Haemostatic properties of human plasma subjected to a sterilizing dose gamma irradiation in the presense of ascorbate. *Blood Coagul Fibrinolysis* 18(3) (2007), pp. 271-7.
[13] Zbikowska, H. Nowak, P. Wachowicz, B. The role of ascorbate and histidine in fibrinogen protection against changes following exposure to a sterilizing dose of gamma-irradiation. *Blood Coagul Fibrinolysis* 18(7) (2007), pp. 669-76.
[14] Grieb, T. Frong, R. Brown, R. Owolabi, T. Maddox, E. McBain, A. Drohan, W. Mann, D. Burgess, W. Effective use of gamma irradiation for pathogen inactivation of monoclonal antibody preparations. *Biologicals* 30 (2002), pp. 207-16.
[15] Gonzalez, E. Moore, F. Holcomb, J, et al. Fresh frozen plasma should be given earlier to patients requiring massive transfusion. *J Trauma* 62 (2007), pp. 112-119.
[16] Hirshberg, A. Gugas, M. Banez, E, et al. Minimizing dilutional coagulopathy in exsanguinating hemorrhage: A computer simulation. *J Trauma* 54 (2003), pp. 454-463.
[17] Tieu, B. Holcomb, J. Schreiber, M. Coagulopathy: its pathophysiology and treatment in the injured patient. *World J Surg* 31(5) (2007), pp. 1055-64.
[18] Exner, R. Tamandl, D. Goetzinger P. et al. Perioperative GLY-GLN infusion diminishes the surgery-induced period of immunosuppression: accelerated restoration of the lipopolysaccharide-stimulated tumor necrosis factor-alpha response. *Ann. Surg.* 237 (2003), pp. 110-5.
[19] Weingartmann, G. Friedrich, P. Mauritz, W. et al. Safety and efficacy of increasing dosages of glycyl-glutamine for total parenteral nutrition in polytrauma patients. *Wien Klin Wochenschr.* 108 (21) (1996), pp. 683-8.
[20] Bakalar, B. Duska, F. Pachl, J. et al. Parenterally administered dipeptide alanyl-glutamine prevents worsening of insulin sensitivity in multiple-trauma patients. *Crit. Care Med* 2006; 34(2) (2006) pp. 381-6.
[21] Spittler, A. Saunter, T. Gornikiewcz, A. et al. Postoperative glycyl-glutamine infusion reduces immunosuppression: partial prevention of the surgery induced decrease in FILA-DR expression on monocytes. *Clin Nutr.* 20(1) (2001) pp. 27-42.
[22] Paauw, J. Davis, A. Taurine supplementation at three different dosages and its effect on trauma patients. *Am J Clin Nutr.* 60 (1994) pp. 203-6.
[23] Chiarla, C. Giovannini, I. Siegel, J. et al. The relationship between plasma taurine and other amino acid levels in human sepsis. *J Nutr.* 130 (2000) pp. 2222-7.
[24] Takahashi, K. Ohyabu, Y. Schaffer S. et al. Taurine prevents ischemia damage in cultured neonatal rat cardiomyocytes. *Adv Exp Med. Biol.* 2000; 483:109-16
[25] Lee, 3. Miyawaki, H. Bobst, E. et al. Improved functional recovery of ischemic rat hearts due to singlet oxygen scavengers histidine and carnosine. *J Mol Cell Cardiol.* 31 (1999) pp. 113-21.
[26] Atan, M. Moochahala, S, Ng, K. et al. Effects of aminoguanidine and L-arginine methyl ester resuscitation following introduction of fluid-percussion injury and severe controlled hemorrhagic shock in the rat brain. *J Neurosurg* 101(1) (2004) pp. 138-44.

[27] Majetschak, M. Cohn, S, Nelson, J. et al. Therapeutic potential of exogenous ubiquitin during resuscitation from severe trauma. *J. Trauma.* 56(5) (2004) pp. 991-9.

[28] Zuckerbraun, B. McCloskey, C. Gallo, D. et al. Carbon monoxide prevents multiple organ injury in a model of hemorrhagic shock and resuscitation. *Shock* 23(6) (2005), pp. 527-32.

The invention claimed is:

1. A composition derived from plasma comprising plasma and a stabilizing effective amount of at least one stabilizer that are freeze dried together, wherein, prior to being freeze-dried, the concentration of platelet particles or the concentration of the protein fraction of the plasma, as compared to untreated plasma, is increased, wherein, prior to being freeze-dried, the platelet particle content is increased, the protein fraction concentration is increased, and the glucose content is decreased as compared to untreated plasma.

2. The freeze-dried plasma composition of claim 1, wherein said at least one stabilizer is one or more amino acids selected from the group consisting of glycine, glutamine, asparagine, taurine and combinations thereof.

3. The composition of claim 2, further comprising an amino acid based buffer which is added prior to freeze-drying.

4. The composition of claim 3, wherein the amino acid based buffer is selected from the group consisting of N,N-Bis (2-hydroxyethyl)glycine, N,N-Bis(2-hydroxyethyl)taurine, glycineamide, and combinations thereof.

5. The composition of claim 3, wherein the amino acid based buffer comprises taurine and N,N-Bis(2-hydroxyethyl) taurine or bicine.

6. The composition of claim 3, wherein said at least one stabilizer is selected from the group consisting of glutamine-containing dipeptides, dipeptides, antioxidants, and combinations thereof.

7. The composition of claim 6 wherein said dipeptide is a glutamine dipeptide or a glycine dipeptide.

8. The composition of claim 6, which is subjected to high dose gamma irradiation and heat treatment as terminal sterilization methods.

9. The composition of claim 3, wherein said at least one stabilizer is selected from the group consisting of glutamine, glutamine-containing dipeptides, glycine dipeptides, taurine, bicine, glycineamide, L-carnosine, aminoguanidine, L-histidine, ubiquitine, vitamin A, vitamin B, vitamin C, vitamin E, and combinations thereof.

10. The composition of claim 3, wherein said at least one stabilizer is an active ingredient beneficial for trauma patients.

11. The freeze-dried plasma composition of claim 1, wherein said at least one stabilizer is taurine.

12. A composition derived from plasma comprising plasma and a stabilizing effective amount of at least one stabilizer that are freeze dried together, wherein, prior to being freeze-dried, the plasma is treated to concentrate particles of about 2 microns or higher and molecules of about 100 kD or higher, wherein treatment comprising passage of the plasma through at least one of a filtration system with a molecular cutoff of about 0.2 microns or higher and a filtration system with a molecular cutoff of about 100 kD or higher.

13. The composition of claim 12, further comprising an amino acid-based buffer which is added prior to freeze-drying.

14. The composition of claim 13, wherein the amino acid-based buffer is selected from the group consisting of N,N-Bis (2-hydroxyethyl)glycine, N,N-Bis(2-hydoxyethyl)taurine, glycineamide, and combinations thereof.

15. The composition of claim 13, wherein the amino acid-based buffer comprises taurine and N,N-Bis(2-hydroxyethyl) taurine or bicine.

16. The composition of claim 12, wherein the at least one stabilizer is selected from the group consisting of glutamine-containing dipeptides, dipeptides, antioxidants, and combinations thereof.

17. The composition of claim 16, wherein said dipeptide is a glutamine-containing dipeptide or a glycine dipeptide.

18. The composition of claim 12, which is subjected to high dose gamma irradiation and heat treatment as terminal sterilization methods.

19. The composition of claim 12, wherein said at least one stabilizer is selected from the group consisting of glutamine, glutamine-containing dipeptides, glycine dipeptides, taurine, bicine, glycineamide, L-carnosine, aminoguanidine, L-histidine, ubiquitine, vitamin A, vitamin B, vitamin C, vitamin E, and combinations thereof.

20. The composition of claim 12, wherein said at least one stabilizer is an active ingredient beneficial for trauma patients.

21. A composition derived from plasma comprising plasma and a stabilizing effective amount of at least one stabilizer that are freeze dried together, wherein, prior to being freeze-dried, the plasma is treated to concentrate particles of about 2 microns or higher and molecules of about 100 kD or higher such that the platelet particle content is increased, the protein fraction concentration is increased, and the glucose content is decreased, as compared to untreated plasma.

22. The composition of claim 21, further comprising an amino acid-based buffer which is added prior to freeze-drying.

23. The composition of claim 22, wherein the amino acid-based buffer is selected from the group consisting of N,N-Bis (2-hydroxyethyl)glycine, N,N-Bis(2-hydroxyethyl)taurine, glycineamide, and combinations thereof.

24. The composition of claim 22, wherein the amino acid-based buffer comprises taurine and N,N-Bis(2-hydroxyethyl) taurine or bicine.

25. The composition of claim 21, wherein the at least one stabilizer is selected from the group consisting of glutamine, dipeptides, antioxidants, glutamine-containing dipeptides, glycine dipeptides, taurine, bicine, glycineamide, L-carnosime, aminoguanidine, histidine, ubiquitine, vitamin A, vitamin B, vitamin C, vitamin E, and combinations thereof.

26. The composition of claim 21, which is subjected to high dose gamma irradiation and heat treatment as terminal sterilization methods.

* * * * *